US00PP24515P2

(12) United States Plant Patent
Greppi

(10) Patent No.: US PP24,515 P2
(45) Date of Patent: Jun. 3, 2014

(54) ***MECARDONIA* PLANT NAMED 'SAKMEC002'**

(50) Latin Name: *Mecardonia hybrida*
Varietal Denomination: SAKMEC002

(71) Applicant: Sakata Seed Corporation, Yokohama (JP)

(72) Inventor: Julian Greppi, Buenos Aires (AR)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 13/815,967

(22) Filed: Mar. 19, 2013

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

(56) References Cited

U.S. PATENT DOCUMENTS

PP18,210 P2 * 11/2007 Miyazaki ..... Plt./263.1

OTHER PUBLICATIONS

Missouri Botanical Garden, http://www.missouribotanicalgarden.org/gardens-gardening/your-garden/plant-finder/plant-details/kc/d808/mecardonia-usmeca67-goldflake.aspx.*

* cited by examiner

*Primary Examiner* — Anne Grunberg
*Assistant Examiner* — Keith Robinson
(74) *Attorney, Agent, or Firm* — Barbara Campbell; Cochran Freund & Young LLC

(57) ABSTRACT

A *Mecardonia* plant particularly distinguished by having a yellow flower color, a compact plant growth habit, long flowering period from spring until late autumn, large flower size, and abundant and continuous flowering, is disclosed.

1 Drawing Sheet

Genus and species: *Mecardonia hybrida.*
Variety denomination: 'SAKMEC002'.

BACKGROUND OF THE NEW PLANT

The present invention relates to a new and distinct variety of *Mecardonia* plant, botanically known as *Mecardonia hybrida*, and hereinafter referred to by the variety name 'SAKMEC002'.

'SAKMEC002' originated from a hybridization made in October 2008 in Buenos Aires, Argentina. The female parent was the proprietary *Mecardonia procumbens* var. *tenella* line named 'AM5-264' (unpatented), having yellow flowers and a compact plant growth habit. The male parent was the proprietary *Mecardonia procumbens* var. *flagellaris* line named '05-25' (unpatented), having yellow flowers, an upright plant habit, and large leaves.

In October 2008, 'AM5-264' and '05-25' were crossed and seeds were obtained. The seeds from the cross were harvested after 30 days. In March 2009, the $F_1$ seed was sown and cultivated in a greenhouse and in the field, and plant lines were produced with yellow flowers and a compact, upright plant growth habit. The $F_1$ plants were evaluated during the spring and summer of 2009 and 2010.

In June 2010, 'G2010-37' was selected for its yellow flower color, compact plant growth habit, long flowering period from spring until late autumn, large flower size, and abundant and continuous flowering. In mid-June 2010, line 'G2010-37' was vegetatively propagated, cultivated and evaluated.

In late September 2010, 'G2010-37' was confirmed to be fixed and stable. 'G2010-37' was propagated and cultivated again in Chogo, Fujisawa, Kanagawa Prefecture, Japan to reconfirm its stability. 'G2010-37' was subsequently named 'SAKMEC002' and its unique characteristics were found to reproduce true to type in successive generations of asexual propagation via vegetative cuttings.

SUMMARY

The following are the most outstanding and distinguishing characteristics of this new variety when grown under normal horticultural practices in Salinas, Calif.

1. Yellow flower color;
2. A compact plant growth habit;
3. Long flowering period, spring until late autumn;
4. Large flower size; and
5. Abundant and continuous flowering.

DESCRIPTION OF THE PHOTOGRAPHS

This *Mecardonia* plant is illustrated by the accompanying photographs which show the plant's overall plant habit including form, foliage, and flowers. The photographs are of a four-month-old plant grown in Salinas, Calif. under greenhouse conditions in the summer of 2012. The colors shown are as true as can be reasonably obtained by conventional photographic procedures.

DESCRIPTION OF THE NEW VARIETY

Figure 1:
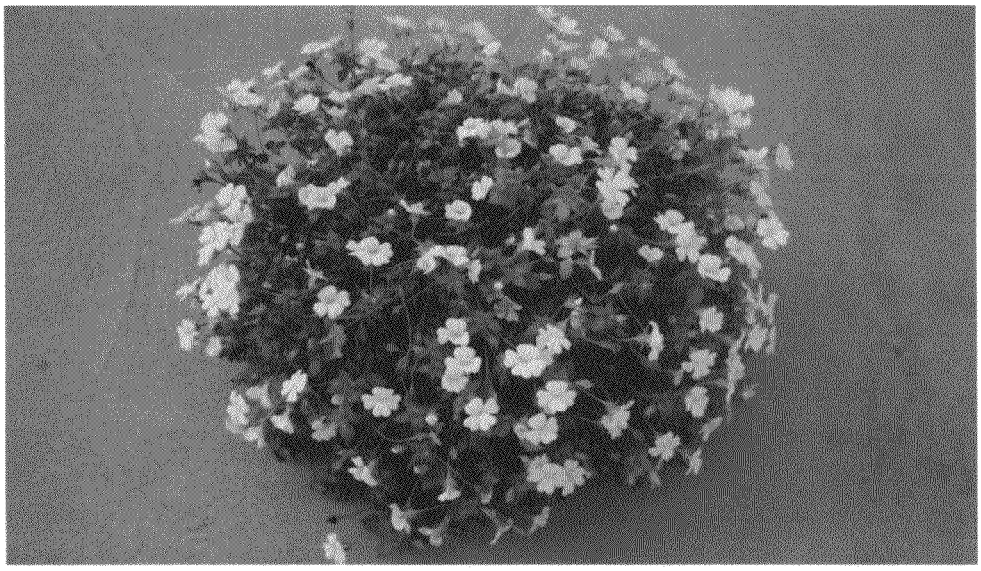
FIG. 1 shows the overall plant habit of the plant grown in a pot.
Figure 2:
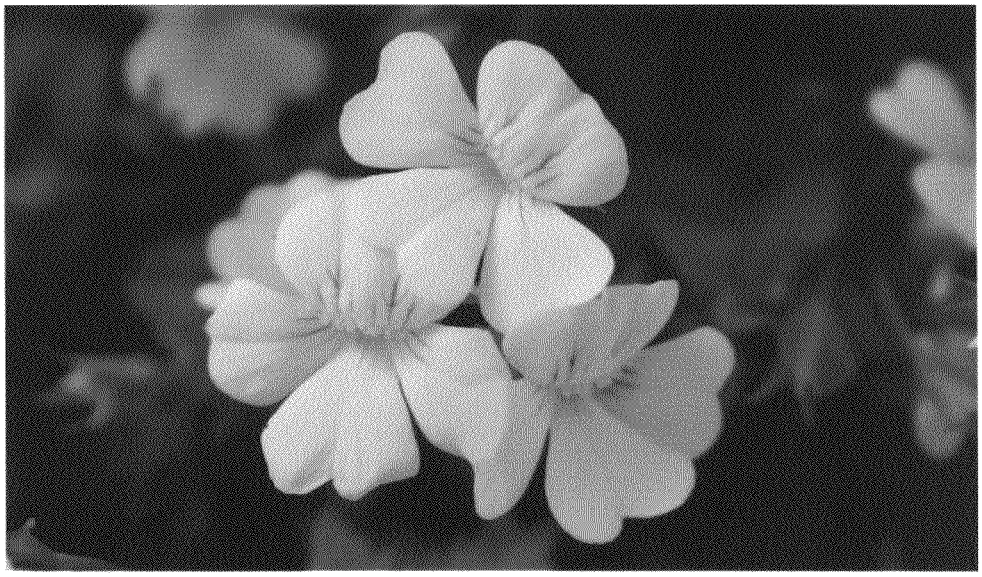
FIG. 2 shows a close-up of the mature inflorescence of the plant.

The following detailed descriptions set forth the distinctive characteristics of 'SAKMEC002'. The data which define these characteristics were collected from asexual reproductions carried out in Salinas, Calif. Data was collected on four-month-old plants grown under greenhouse conditions in Salinas, Calif. in the summer of 2012. Color references are to The R.H.S. Colour Chart of The Royal Horticultural Society of London (R.H.S.), 4th edition (2001).

Classification:

*Family*.—Plantaginaceae.

*Botanical*.—*Mecardonia hybrida*.

*Common name*.—*Mecardonia*, Axilflower.

*Designation*.—'SAKMEC002'.

Parentage:

*Female parent*.—Proprietary hybrid *Mecardonia* line 'AM5-264' (unpatented).

*Male parent*.—Proprietary hybrid *Mecardonia* line '05-25' (unpatented).

Growth:

*Time to produce a rooted cutting*.—About 6 weeks. The terminal 1.0 to 1.5 inches of an actively growing stem was excised. The vegetative cuttings were propagated in five to six weeks. The base of the cuttings were dipped for 1 to 2 seconds in a 1:9 solution of Dip 'N Grow (1 solution: 9 water) root inducing solution immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 20 cm diameter plastic pots in a glass greenhouse located in Salinas, California. Pots contained a peat moss-based growing medium. Soluble fertilizer containing 20% nitrogen, 10% phosphorus and 20% potassium was applied once a day or every other day by overhead irrigation. Pots were top-dressed with a dry, slow release fertilizer containing 20% nitrogen, 10% phosphorus and 18% potassium. The typical average air temperature was 24° C.

Plant description:

*Habit and form*.—Compact, freely branching, and moderately dense.

*Life cycle*.—Annual.

*Height* (*from soil line to top of foliage*).—9.0 cm.

*Spread*.—32.0 cm.

*Flowering requirements*.—Will flower from spring until late autumn at temperatures above 13° C.; will bloom from planting to frost.

Branches:

*General description*.—Circular in cross-section; dull in appearance.

*Length*.—14.0 cm.

*Diameter*.—0.1 cm.

*Internode length*.—1.5 cm.

*Color*.—RHS 143B (Green).

*Surface texture*.—Glabrous.

*Anthocyanin color*.—Absent.

*Strength*.—Moderate.

Leaves:

*Arrangement and appearance*.—Opposite, simple, with decurrant leaf attachment.

*Shape*.—Elliptic.

*Apex*.—Acute.

*Base*.—Attenuate.

*Margin*.—Serrate.

*Surface texture* (*both surfaces*).—Smooth, glabrous.

*Length*.—1.3 cm.

*Width*.—0.8 cm.

*Color*.—Upper surface: RHS 147A (Yellow-Green). Lower surface: RHS 137B (Green).

*Venation*.—Pinnate.

*Venation color* (*both surfaces*).—Closest to RHS 144B (Yellow-Green).

*Petiole length*.—0.2 cm.

*Petiole diameter*.—0.1 cm.

*Petiole color*.—Closest to RHS 144B (Yellow-Green).

*Petiole texture*.—Smooth, glabrous.

*Fragrance*.—Absent.

Inflorescence:

*Inflorescence type*.—Solitary axillary flowers that face mostly upward to outwardly; freely flowering with approximately 250 to 300 flowers open at any given time.

*Flowering habit*.—Long flowering period from spring until late autumn.

*Time to bloom from propagation*.—10 weeks.

*Lastingness of individual blooms on the plant*.—5 days.

*Fragrance*.—Absent.

Peduncle:

*Length*.—4.0 cm.

*Diameter*.—0.1 cm.

*Color*.—RHS 145B (Yellow-Green).

*Surface appearance and texture*.—Smooth, glabrous.

*Strength*.—Moderately strong, wirey.

Corolla:

*Shape*.—Composed of a single whorl with four petals; petals are curved inward at mid-vein.

*Flower diameter*.—1.5 cm.

*Flower depth*.—0.5 cm.

*Flower shape*.—Ovate.

*Petals*.—Shape: Ovate. Apex: Rounded to emarginated, cleaved. Base: Fused. Margin: Entire. Surface texture (both surfaces): Smooth, glabrous, upper petal with tiny hairs at petal base. Length: 1.2 cm. Width: 1.2 cm. Color of lobes: Upper surface: Closest to RHS 9A (Yellow) with RHS N186A veins (Greyed-Purple). Lower surface: Closest to RHS 9A (Yellow).

Calyx:

*Arrangement*.—Composed of 5 sepals per flower.

*Sepals*.—Shape: Elliptical. Apex: Obtuse. Margin: Entire. Base: Truncate. Color (both surfaces): RHS 143B (Green). Length: 0.5 cm. Diameter: 0.3 cm. Texture (both surfaces): Smooth, glabrous.

Reproductive organs:

*Stamen number*.—4, free.

*Filament length*.—0.5 cm.

*Filament color*.—RHS 145C (Yellow-Green).

*Anther shape*.—Oval, bi-lobed.

*Anther color*.—RHS 155D (White).

*Anther length*.—0.1 cm.

*Pollen color*.—RHS 155D (White).

*Pollen amount*.—Abundant.

*Ovary color*.—RHS N144D (Yellow-Green).

*Pistil number*.—1 (per inflorescence).

*Pistil length*.—0.3 cm.

*Stigma color*.—RHS N144D (Yellow-Green).

*Stigma shape*.—Ovate.

*Style length*.—0.15 cm to 0.2 cm.

*Seed production*.—Absent.

Disease and insect resistance: None observed; not known to have resistance to pathogens and pests common to *Mecardonia* plants.

COMPARISON WITH PARENTAL LINES AND KNOWN VARIETY

'SAKMEC002' is a new and unique variety of *Mecardonia* owing to its yellow flower color, compact plant growth habit, long flowering period from spring until late autumn, large flower size, and abundant and continuous flowering. 'SAKMEC002' is distinguished from its parents mainly by flower color as shown in Table 1 below:

TABLE 1

Comparison with Parental Lines

| Characteristic | 'SAKMEC002' | Female Parent 'AM5-264' | Male Parent '05-25' |
|---|---|---|---|
| Flower color | Yellow | Yellow | Yellow |
| Plant growth habit | Compact | Compact | Upright |
| Leaf size | Large | Medium | Large |

'SAKMEC002' is a new and unique variety of *Mecardonia* owing to its yellow flower color, compact plant growth habit, long flowering period from spring until late autumn, large flower size, and abundant and continuous flowering. 'SAKMEC002' is most similar to the commercial *Mecardonia* variety 'USMECA8205' (U.S. Plant Pat. No. 22,871); however there are differences as described in Table 2 below.

TABLE 2

Comparison with Similar Variety

| Characteristic | 'SAKMEC002' | 'USMECA8205' |
|---|---|---|
| Flower petal color, upper surface | Closest to RHS 9A (Yellow) with upper petal lobes having veins of RHS N186A (Greyed-Purple) | Close to RHS 11A (Yellow) |
| Plant growth habit | Compact | Low mounding to trailing |

I claim:

1. A new and distinct variety of *Mecardonia* plant as shown and described herein.

* * * * *